(12) United States Patent
Sers

(10) Patent No.: US 7,824,181 B2
(45) Date of Patent: Nov. 2, 2010

(54) CUSTOM-FIT IMPLANT SURGERY GUIDE AND ASSOCIATED MILLING CUTTER, METHOD FOR THEIR PRODUCTION, AND THEIR USE

(75) Inventor: Laurent Sers, Cannes (FR)

(73) Assignee: Materialise Dental NV, Heverlee (BE)

( * ) Notice: Subject to any disclaimer, the term of this patent is extended or adjusted under 35 U.S.C. 154(b) by 969 days.

(21) Appl. No.: 11/579,533

(22) PCT Filed: May 3, 2005

(86) PCT No.: PCT/FR2005/001109

§ 371 (c)(1),
(2), (4) Date: Nov. 3, 2006

(87) PCT Pub. No.: WO2005/120385

PCT Pub. Date: Dec. 22, 2005

(65) Prior Publication Data

US 2008/0287953 A1 Nov. 20, 2008

(30) Foreign Application Priority Data

May 4, 2004 (FR) .................................. 04 04789

(51) Int. Cl.
*A61C 3/02* (2006.01)
(52) U.S. Cl. ............................. 433/76; 433/176; 606/87
(58) Field of Classification Search .................. 30/165, 30/388–391; 83/15, 666, 651, 701; 433/72–74, 433/165–166, 176; 606/80, 87, 96–97, 167–183; 407/33–34, 53–54, 66–69, 99
See application file for complete search history.

(56) References Cited

U.S. PATENT DOCUMENTS

| | | | | |
|---|---|---|---|---|
| 3,474,537 A | * | 10/1969 | Christensen | 433/174 |
| 3,925,892 A | * | 12/1975 | Juillet | 433/176 |
| 4,084,318 A | * | 4/1978 | McEachern | 433/174 |
| 4,722,687 A | * | 2/1988 | Scortecci | 433/165 |
| 5,098,436 A | * | 3/1992 | Ferrante et al. | 606/88 |
| 5,320,529 A | * | 6/1994 | Pompa | 433/76 |
| 5,439,381 A | * | 8/1995 | Cohen | 433/173 |
| 5,641,287 A | * | 6/1997 | Gittleman | 433/75 |
| 5,833,693 A | * | 11/1998 | Abrahami | 606/96 |
| 5,967,777 A | | 10/1999 | Klein | |

(Continued)

FOREIGN PATENT DOCUMENTS

BE  1008372  4/1996

(Continued)

*Primary Examiner*—Thomas C Barrett
*Assistant Examiner*—Larry E Waggle, Jr.
(74) *Attorney, Agent, or Firm*—William H. Holt

(57) ABSTRACT

The invention relates to a custom-fit implantable surgical guide (1) and an associated milling tool (4), which is positioned in straddling on the alveolar ridge (7) of a maxillary or mandible arch (2) and comprises at least one drilling barrel (11) for axially guiding said milling tool (4), wherein said barrel (11) is laterally open and at least one part of the internal surface thereof (17) and at least one part of the external surface of the milling tool (4) interact and axially maintain the entire milling tool (4) with respect to the barrel (11). Said invention makes it possible to carry out high precision osteotomies for lateral insertion dental implants.

20 Claims, 4 Drawing Sheets

U.S. PATENT DOCUMENTS

2005/0170311 A1 * 8/2005 Tardieu et al. ................ 433/76

FOREIGN PATENT DOCUMENTS

| BE | 1008372 A3 * | 4/1996 |
| DE | 4026011 | 2/1992 |
| FR | 2032287 | 11/1970 |
| FR | 2302715 | 10/1976 |
| FR | 2561907 | 10/1985 |
| FR | 2870714 A1 * | 12/2005 |
| WO | 9926540 | 6/1999 |
| WO | 0207633 | 1/2002 |
| WO | WO 0207633 A2 * | 1/2002 |

* cited by examiner

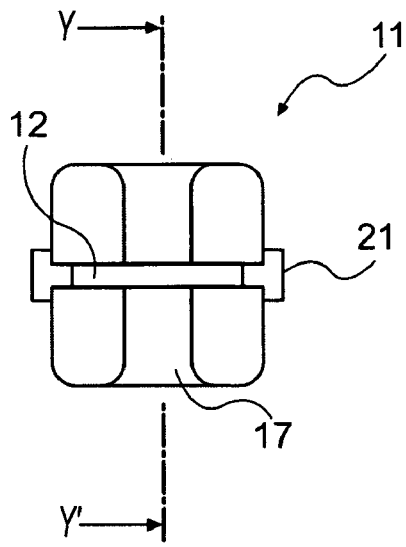
FIG. 2a
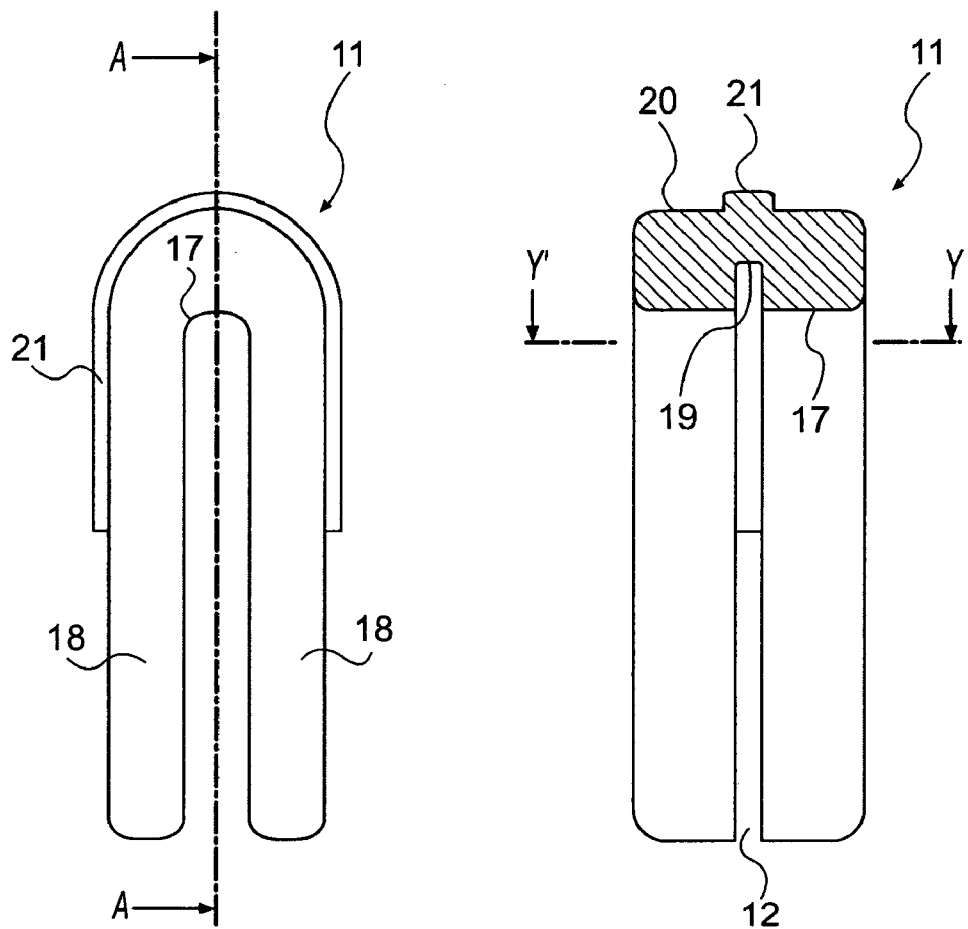
FIG. 2b     FIG. 2c

CUSTOM-FIT IMPLANT SURGERY GUIDE AND ASSOCIATED MILLING CUTTER, METHOD FOR THEIR PRODUCTION, AND THEIR USE

TECHNICAL FIELD OF THE INVENTION

The present invention relates to a custom-fit implant surgery guide, the associated milling cutter, method for their production, and their use.

TECHNICAL BACKGROUND OF THE INVENTION

For aesthetic considerations or therapeutic reasons the missing teeth in a seriously diseased set of teeth of a patient often have to be replaced by prostheses. The most commonly used prostheses are still tooth-supported or gum-supported prostheses, although the emplacement of prostheses anchored and fixed in the mandible or the maxilla of the patient by means of one or more implants screwed into holes drilled in the bone tissue, or simply inserted into osteotomies, is being developed.

Endo-osseous dental implants are divided into various categories according to their shapes and methods of insertion.

A first category consists of axial implants, or more generally of implants involving vertical insertion on the alveolar ridge. The most commonly used system of screw-in axial implants is the so-called "Branemark" system named after its inventor, who disclosed this system in France in Application FR 2,032,287 published on 27 Nov. 1970.

A second category consists of implants inserted laterally into the jawbones. These implants generally include a vertical shank intended to support the prosthesis and a seating perpendicular to the shank, consisting of a plate or one or more discs. For example, an implant of this type comprising a perforated rectangular plate is described in French Patent Application FR 2,302,715 published on 1 Oct. 1976 in the names of B. Clunet-Coste and J. Maneuf.

French Patent Application FR 2,561,907 published on 4 Oct. 1985 in the name of G. Scortecci discloses a lateral insertion implant the seating of which alternatively consists of a disc.

This second type of implants has numerous advantages over the first type, particularly when the bone volume available for the implantation is reduced, or when the opening of the buccal cavity is too small to permit an axial implant. A major advantage is the possibility of an immediate loading of the implant by the prosthesis.

However, in order to achieve this object, the osteotomy of complementary shape to the implant must be made with a very high degree of precision so as to avoid any play that could subsequently lead to a rejection phenomenon.

German Patent Application No. DE 4,026,011 published on 20 Feb. 1992 in the name of G. Lakos describes a process and a device enabling the dental surgeon's movements to be guided. This device consists of an adjustable abutment or lug fixed on the one hand to the drill turbine and resting on the other hand on the osseous ridge. In this way the milling cutter wheel is positioned at the desired height and its lateral penetration into the bone is restricted.

In the case of axial implants it is known to employ modern medical imaging techniques combined with robotic techniques so as to simulate in three dimensions on a computer the positioning of this type of implants before any surgical intervention, and to make a drilling template that will guide the dental surgeon during the operation. The implementation of these techniques has significantly increased the chance of obtaining good aesthetic results, while reducing the risk of post-operation complications.

A process and a device of this type for determining the ideal emplacement of an axial implant, and designed for the precise positioning of the latter, are described in U.S. Pat. No. 5,320,529, in the name of D. Pompa, published on 14 Jun. 1994. According to this procedure a stereolithographic model of the jawbone is produced from tomographic sections, and enables the dental surgeon to simulate on this model the positioning of the prostheses. A surgical guide is made by molding a model of the bone and radio-opaque models of the implants in situ, provided with their implant supports. Drilling barrels of interior diameters corresponding to drill bits of different sizes are then placed in the casts or impressions of the implant carriers.

The drilling template described in the International Application WO 99/26540 in the name of M. Klein et al. published on 3 Jun. 1999, adopts the above principle of using drilling barrels of different diameters inserted into bores of a single diameter, virtually the only difference being that these are inserted into cylinders that are themselves placed in bores drilled directly in the scannographic guide by a digitally controlled drilling machine starting from scanner data.

The process for making models of parts of the human body from digital images disclosed by Materialise N.V. in Belgian Patent BE 1,008,372 published on 2 Apr. 1996, and applied in particular to computer-aided implantology, avoids the molding stage by allowing not only the models of the mandible and maxilla, but also the dimensionally accurate surgical guides corresponding to any required implant plan, to be produced directly by stereolithography.

Starting from the scanner data, the implantologist prepares a virtual implant plan by means of software designed for implementing the above process, and sends the results to a dental laboratory responsible for converting these data into actual drilling templates. During the course of the operation, a template is positioned on the alveolar crest; thanks to the complex shapes of the jawbones and teeth, the positioning of the template is unique and stable. The templates contain implantable stainless steel cylinders that form physical guides for the drills during surgery and enable the drilling axes to be controlled in an optimum manner. Several templates are produced with cylinders of different diameters, enabling the drilling sequence specific to each implant to be taken into account and allowing the dental surgeon to adapt to the circumstances of each individual case. When the site is ready, the implants are inserted in the normal way by means of the implant carrier.

It thus follows from the documents cited above that various computer-aided implantology systems for the emplacement of axial implants are known from the prior art.

However, none of these systems permits the use of lateral insertion implants. Moreover, neither does there exist any surgical guide capable of realizing osteotomies specific to this particular type of implants, nor is there any process for inserting the latter in situ using such a guide.

GENERAL DESCRIPTION OF THE INVENTION

The present invention thus relates to a custom-fit implant surgery guide and the associated milling cutter, the features of which are intended to fill an important gap in the prior art.

The object of the invention is more specifically a surgical guide of the type placed on both sides on the alveolar ridge of a maxillary or mandibular arch, and comprising at least one drilling barrel capable of axially guiding a milling cutter.

The surgical guide according to the invention is remarkable on the one hand in that this barrel is open laterally, and on the other hand in that at least a part of the internal surface of the barrel and at least a part of the external surface of the milling cutter co-operate with one another and ensure the total axial stability of the milling cutter with respect to the barrel.

Preferably the barrel comprises a transverse slit extending in a substantially medial plane perpendicular to its axis. The drive shaft of the corresponding milling cutter comprises a collar, the slit of the barrel and the collar of the milling cutter co-operating with one another.

Alternatively, according to a variant of the invention the drive shaft of the milling cutter comprises two collars surrounding the barrel.

According to another embodiment, the internal surface of the barrel comprises a radially grooved part and the drive shaft of the milling cutter comprises a ringed part. This grooved part is complementary to the ringed part of the milling cutter and co-operates with the latter.

Most advantageously, the surgical guide according to the invention has at least one barrel that extends laterally in a direction substantially perpendicular to the longitudinal axis of the guide. At least one part of the drive shaft of the associated milling cutter itself acts as a milling cutter, and preferably comprises longitudinal splines, the edges of which are cutting edges. The milling cutter also preferably comprises at least one toothed wheel.

The surgical guide according to the invention is also remarkable on the one hand in that it contains at least one laterally open bore comprising an insert, and on the other hand in that at least a part of the internal surface of this insert and a part of the external surface of the barrel co-operate with one another and ensure the axial stability of the barrel with respect to this bore.

Preferably the internal surface of the insert comprises a groove extending in a substantially medial plane perpendicular to its axis, and the external surface of the barrel comprises a medial spline complementary to this groove. Advantageously the barrel and the insert have the general shape of a bracket, with a substantially U-shaped cross-section. The branches of this U then extend laterally, substantially in a plane parallel to the alveolar ridge. The axis perpendicular to this ridge, and passing through the centre of the rounded part of the U, coincides in this case with the axis of the milling cutter.

The present invention also relates to a method for producing the custom-fit implant surgery guide and the associated milling cutter described above. In a known manner, the method according to the invention comprises the following stages:
a) placement of a scannographic guide in the patient's mouth,
b) acquisition by computer of the scanner data of this scannographic guide and of the patient's mandible or maxilla,
c) computer simulation of the mandible or maxilla using the scanner data,
d) computer generation, under the control of the dental surgeon, of implant plan parameters using this simulation,
e) computer control, using the plan parameters, of a device for making a template intended to reproduce the shape of the alveolar ridge and exhibiting bores having precalculated axes and positions,
f) fixing guide inserts in the bores of the template,
g) insertion in these inserts of drilling barrels arranged so as to control the direction and depth of penetration of a milling cutter.

The method according to the invention is distinguished from the prior art by the fact that:
the implant plan is adapted to implants inserted laterally with respect to the alveolar ridge,
the bores of the template, the inserts and the barrels are provided with lateral opening with respect to this ridge,
the milling cutter that is used is provided with axial stability means co-operating with the barrels.

A stereolithographic process is advantageously used to produce the template. The inserts are preferably bonded in the template. The milling cutter is advantageously produced by forging a single piece of metal in the course of a specific stage.

The custom-fit implant surgery guide and the associated milling cutter according to the invention are preferably used in a process for the placement in situ of dental implants of the type comprising the following stages:
a) placement of a scannographic guide in the patient's mouth,
b) acquisition by computer of the scanner data of this scannographic guide and of the patient's mandible or maxilla,
c) computer simulation of the mandible or maxilla using the scanner data,
d) computer generation, under the control of the dental surgeon, of implant plan parameters using this simulation,
e) computer control, using the plan parameters, of a device for making a template intended to reproduce the shape of the alveolar ridge and exhibiting bores having precalculated axes and positions,
f) fixing guide inserts in these bores,
g) insertion in these inserts of drilling barrels arranged so as to control the direction and depth of penetration of a milling cutter,
h) formation of osteotomies intended to receive the implants in the patient's mandible or maxilla, by means of the milling cutter guided by the barrels,
i) placement in situ between the inserts of the implants in the osteotomies.

Within the specific scope of the invention the planning is adapted to lateral insertion implants with respect to the alveolar ridge and the milling cutter is introduced laterally with respect to this ridge into the barrels.

Advantageously the implants are introduced by percussion into the osteotomies, all the while being guided laterally with respect to the alveolar ridge by the inserts of the guide according to the invention.

Preferably the implants are of the type comprising at least one disc arranged axially on a shank intended to carry a prosthesis.

A great advantage is obtained by using the surgical guide according to the invention, on account of the fact that the implants are loaded by the prostheses immediately after their emplacement.

These essential features described above clearly show the dental surgeon the advantages provided by the custom-fit implant surgery guide, the associated milling cutter, the method for their production and their use according to the invention, compared to the prior art.

The details of the invention, and in particular of examples of advantageous selections of dimensional characteristics of the constituent elements of the guide and of the milling cutter, are given in the following description in conjunction with the accompanying drawings. It should be noted that these drawings serve only to illustrate the text of the description and do not constitute any sort of restriction on the scope of the invention.

BRIEF DESCRIPTION OF THE DRAWINGS

FIGS. 2a, 2b and 2c are respectively a front view, a view from above and a longitudinal sectional view along A-A of a drilling barrel of the guide according to the invention.

DESCRIPTION OF PREFERRED FORMS OF THE INVENTION

Figure 1:
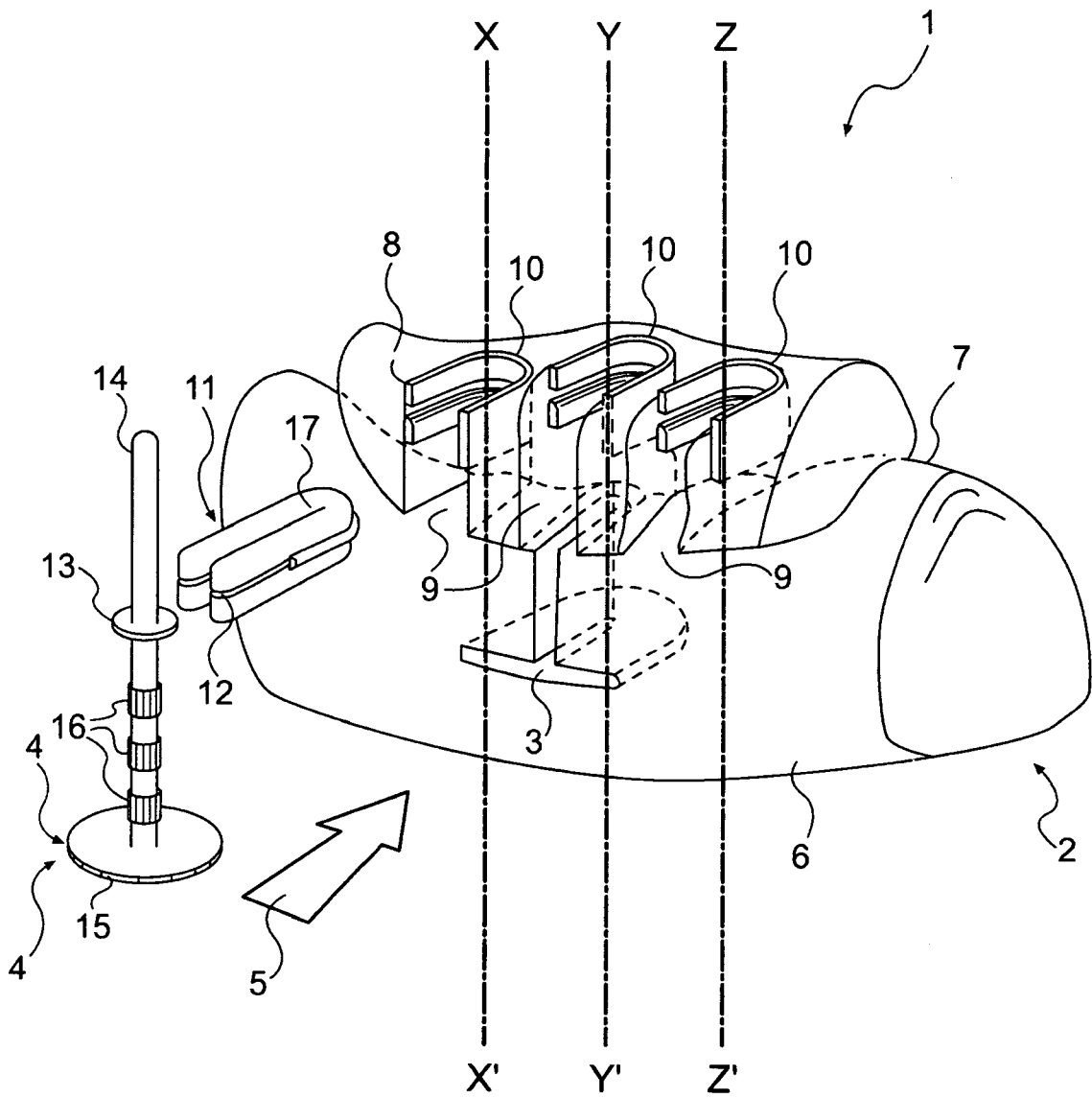
FIG. 1 is an exploded view of a custom-fit implant surgery guide and of an associated milling cutter according to the invention. The guide is shown in situ on an alveolar ridge. A typical osteotomy of the mandible is also shown.

FIG. 1 shows by way of example a custom-fit implant surgery guide 1 prepared for the emplacement of three implants of the "disc implant" type in a mandibular bone arch 2. This type of endo-osseous implant, comprising one or more discs fixed axially on a shank intended to support a prosthesis, requires the preparation of one or more T-shaped osteotomies 3 for its emplacement. One of such osteotomies 3 adapted for the emplacement of an implant having a single disc is shown in FIG. 1.

The osteotomy 3 is normally performed by the dental surgeon using a milling cutter wheel 4 engaged laterally according to 5 in the extra-buccal wall 6 of the mandible 2. The axis and the depth of the osteotomy 3 should satisfy the constraints of the implant plan. The osteotomy plane 3 should also be accurately located with respect to the alveolar ridge 7.

The surgical guide 1 placed on both sides on the alveolar ridge 7 and the associated milling cutter 4 according to the invention enable the dental surgeon to achieve a very high operational precision.

The guide 1 consists of a template 8 obtained by a stereolithographic process using scanner data of the patient and the implant simulation.

The template 8 comprises three bores 9 of axes XX', YY', ZZ' corresponding to the axes of the future implants. These bores 9 are open laterally, to the exterior of the buccal cavity, and are provided with inserts 10, shaped in the form of brackets, bonded to the interior. The inserts 10 are made of a titanium alloy, normally of TA6V.

These inserts 10 surround drilling barrels 11 (only one of which is shown in FIG. 1), similarly U-shaped and of steel such as INOX 316L, intended to ensure the guidance and axial stability of the milling cutter 4. For this purpose each of the barrels 11 has a transverse slit 12 co-operating with a collar 13 of the drive shaft 14 of the milling cutter 4.

The shaft 14 of the milling cutter 4 comprises between the collar 13 and the toothed wheel 15 zones 16 with splines, the edges of which are cutting edges. The milling cutter 4 displaced laterally according to 5 in the direction of the mandible 2, the movement then being guided by the collar 13 sliding in the slit 12 of the drilling barrel 11 and being restricted by the semi-cylindrical surface 17 of the base of the barrel 11, consequently enables the T-shaped osteotomy to be formed having the nominal parameters of the implant plan.

FIGS. 2, 3 and 4 show more specifically the mechanical characteristics of an insert, of a barrel and of a milling cutter, the totality of which enables the desired result to be achieved.

The front view of the barrel 11 of FIG. 2a clearly shows the transverse slit 12 in a medial plane perpendicular to the axis YY'.

The view from above of FIG. 2b clearly shows the U-shape of the barrel 11, the two branches 18 of which extend laterally beyond the bore 9 of the template 8 and thereby enable the milling cutter to be guided during its approach to the bone wall 6.

Figure 3A:
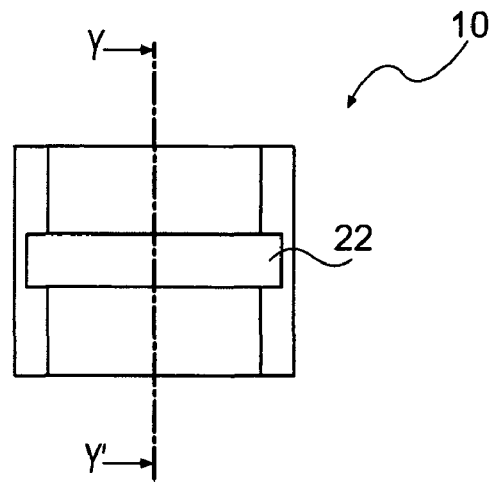
FIGS. 3a, 3b and 3c are respectively a front view, a view from above and a longitudinal sectional view along B-B of an insert intended to receive the barrel shown in FIGS. 2a, 2b and 2c.
Figure 3B:
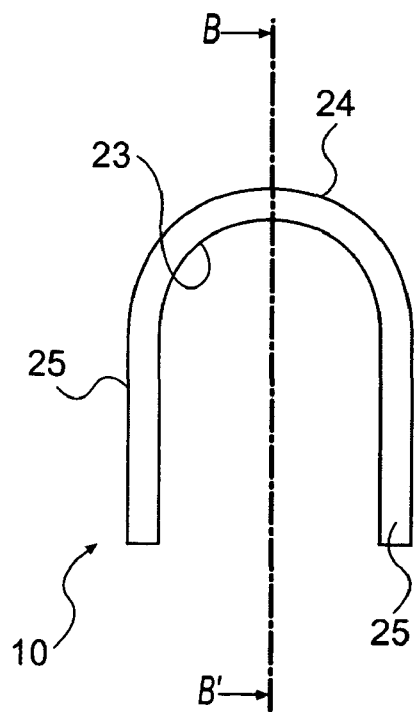
Figure 3C:
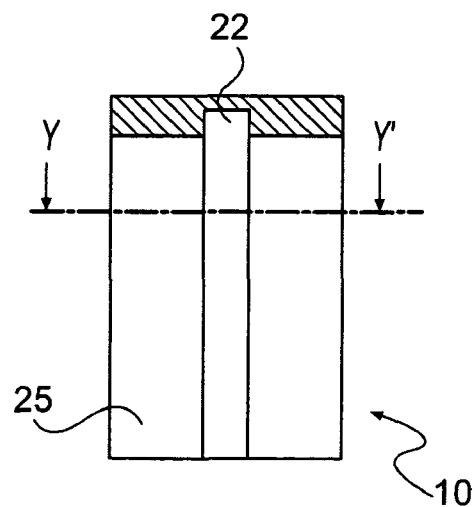

The sectional view along AA of FIG. 2c clearly shows the shape of the base of the barrel 11: its semi-cylindrical internal surface 17 having an annular groove 19 is complementary to the oppositely facing part of the shaft 14 and of the collar 13 of the milling cutter 4, when the latter is fully engaged. The semi-cylindrical external surface 20 of the barrel has a medial spline 21 complementary to a medial groove 22 on the internal surface 23 of the curved part of the insert 10, as can be seen in FIGS. 3a, 3b and 3c.

The external dimensions of the inserts are compatible with the software of existing implant plans.

An insert 10 preferably has a length of 8.00 mm and a height of 5.00 mm. Its semi-cylindrical external surface 24 (at the level of the curved part of the U) has a diameter of 6.00 mm. The oppositely facing semi-cylindrical internal surface 23 has a diameter of 4.50 mm. The branches 25 of the U typically have a thickness of 0.75 mm. The internal medial groove 22 of rectangular cross-section has a depth of 0.43 mm and a width of 1.05 mm.

The barrels 11 have dimensions adapted to those of the inserts 10 and milling cutters 4 that are used. A barrel 11 preferably has a length of 14.25 mm and a height of 5.00 mm. The diameter of the semi-cylindrical internal surface 17 of the base of the barrel 11 has a diameter of 1.54 mm. The diameter of the semi-cylindrical external surface 20 has a diameter of 4.50 mm, corresponding to the external diameter of this part of the insert 10. The branches 18 of the barrel 11 have a thickness of 1.48 mm. The external spline 21 is of rectangular cross-section and has a height of 0.43 mm and a width of 1.00 mm. The transverse slit 12 preferably has a width of 0.33 mm.

Figure 4A:
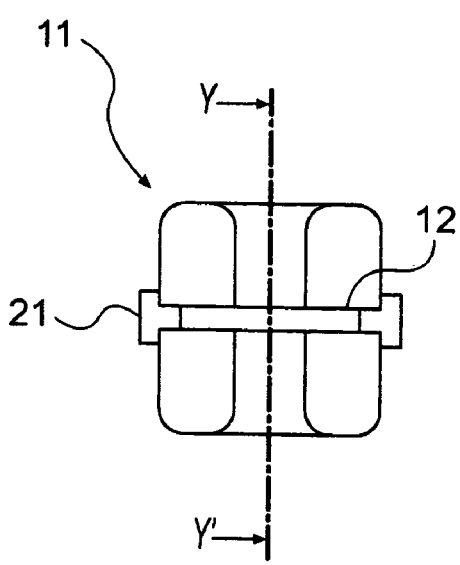
FIGS. 4a, 4b and 4c show respectively the preferred mode of implementation of a custom-fit implant surgery guide and of the associated milling cutter according to the invention, as well as two variant embodiments.
Figure 4A:
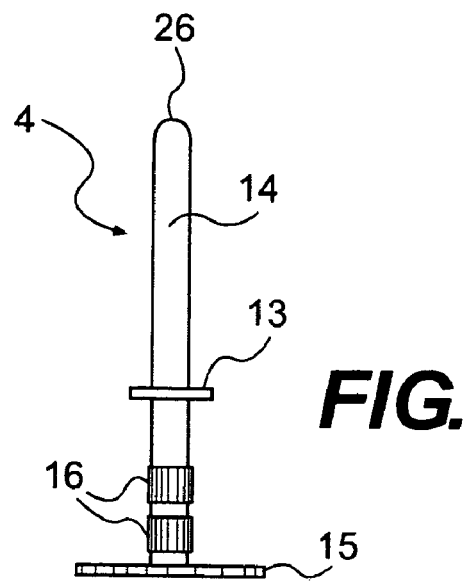

FIG. 4a shows a milling cutter adapted to the above barrel 11. The driving shaft thus preferably has a diameter of 1.50 mm, slightly less than the diameter of the semi-cylindrical internal surface 17 of the base of the barrel 11.

The height of 13.75 mm between its collar 13 and the end 26 of the shaft 14 intended to be inserted into the tool holder is standard.

The collar 13 preferably has a diameter of 3.50 mm, corresponding to the diameter of the annular groove 19 of the base of the barrel 11, and a thickness of 0.30 mm, which is slightly less than the thickness of the slit 12 of the barrel 11.

The height of the part of the shaft 14 between the collar 13 and the end supporting the toothed wheel 15 depends on the relevant circumstances. For a set of milling cutters adapted to conventional cases, this height is of the order of 8.75 mm, 14.75 mm or 20.75 mm.

Similarly, the diameter of the toothed wheel 15 may adopt different values: 3.05 mm, 6.05 mm, 7.05 mm, 8.05 mm, 9.05 mm, 10.05 mm, 12.05 mm, 15.05 mm or 20.05 mm. The thickness of the toothed wheel is preferably 0.30 mm.

It goes without saying that the dimensions of the shaft 14 and of the toothed wheel 15 are not critical. Conversely, the respective dimensions of the contacting parts 17, 19, 13, 14 of the barrel 11 and of the milling cutter 4 are critical.

Figure 4B:
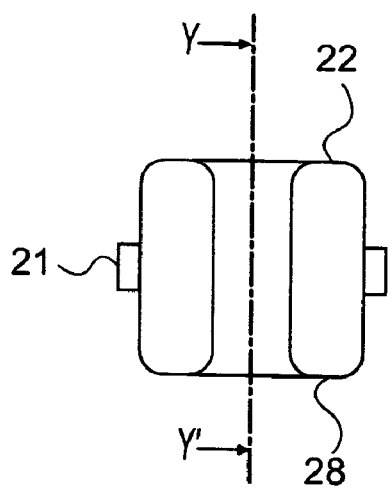
Figure 4B:
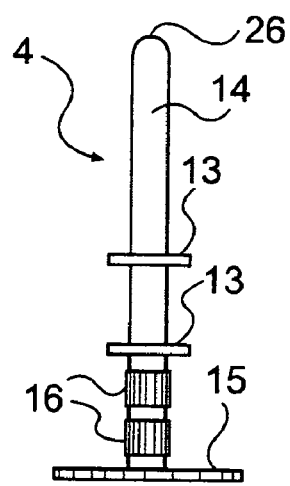
Figure 4C:
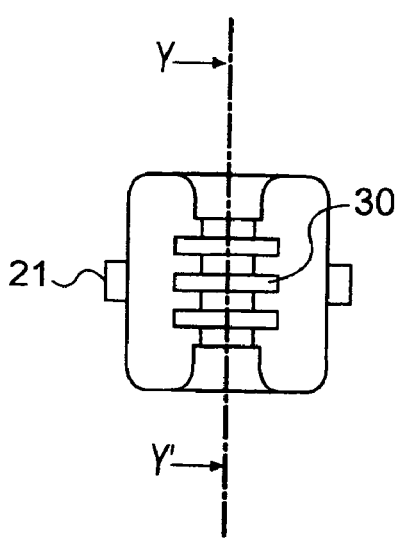
Figure 4C:
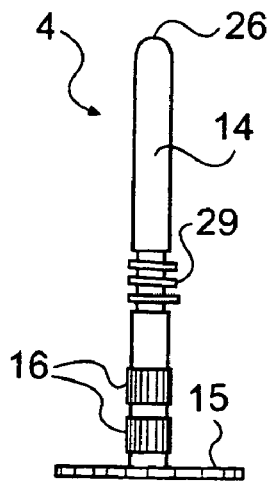

Embodiments of the pair consisting of barrel 11 and milling cutter 4 are shown in FIGS. 4b and 4c.

FIG. 4b shows a variant in which the guidance and axial stability of the milling cutter 4 by the barrel 11 are achieved thanks to two collars designed to surround the upper surface 27 and the lower surface 28 of the barrel. The advantage of this variant is that it is not necessary to make a slit 12 in the barrel 11. The disadvantage is that two collars 13 are required. The external surface 20 and the spline 21 of this barrel 11 are identical to those of the barrel of FIGS. 2a, 2b, 2c and 4a, which enables the same insert 10 to be used.

FIG. 4c shows another embodiment in which a part 29 of the shaft 14 is ringed. This ringed part 29 co-operates with complementary circular grooves 30 provided in the inner surface 17 of the base of the barrel 11, when the milling cutter 4 is fully engaged, or with rectilinear grooves 30 made in the lower surface of each of the branches 18 of the barrel 11 when the milling cutter 4 is inserted into the lateral opening of the barrel 11. The advantage of this variant is a simpler machining of the shaft 14 of the milling cutter 4. The disadvantage is a much greater fragility.

The template 8 is made by employing the known computer-aided implantology procedures perfected for axial implants, but adapted in an original manner for the emplacement of lateral insertion implants.

In the known procedures of this type, the dental surgeon having at his disposal a computer-aided implantology system decides with the patient in the course of a preliminary stage the emplacement and positioning of implants.

A scannographic guide is placed in the patient's mouth, and the guide then runs its scanner in a conventional manner. This guide comprises radio-opaque markers that will subsequently enable the reference benchmarks of the radiological images obtained by computer during the course of this stage to be matched to the actual prostheses.

Following this examination, the scanner data of the scannographic guide and of the jaw 2 of the patient are sent to a dental laboratory, which processes and prepares the raw data before they are sent to the implantologist.

The software available to the dental surgeon carries out a virtual reconstruction of the mandible 2 or maxilla of the patient using the prepared scanner data. This computer simulation enables an implant plan to be created by visualizing the emplacements of the future implants. The parameters of the plan will be sent back to the dental laboratory for the preparation of the template 8 provided with inserts 10.

In a manner known per se, the dental laboratory uses during the course of this phase the received data in order to control a stereolithographic device, which has the advantage over the digital milling cutter of being able to produce pieces comprising closed cavities.

The dental laboratory bonds insets 10 to the interior of the bores 9 of the template 8 and sends the latter, together with an actual model of the jaw 2, to the implantologist. In the known case of implant systems for axial implants, these inserts are cylinders of standard size, which is chosen depending on the type of implants that will be put in place.

During the following stage, that is to say during the surgical procedure involving the emplacement of the implants per se, the dental surgeon uses the template 8 in order to make the osteotomies 3 intended to receive the implants, each at the desired point and in the appropriate direction as specified in the implant plan. For this purpose, in the known case of axial implants the dental surgeon inserts barrels 11 of cylindrical drills into the guide inserts 10 of the template 8. These drilling barrels 11 restrict the depth of penetration of the miffing cutter 4 or of the drill.

The computer-aided implantology systems are complex sets of procedures, materials and equipment optimized according to the objective that is to be achieved. It follows that the features of each of the elements of these systems are highly interdependent, and lead to standards that are the result of the generalization of certain "proprietary systems" marketed by the largest manufacturers of medical equipment.

In order to be widely accepted, any new device must be based on these standards. The procedure involved in the production of the custom-fit implant surgery guide 1 according to the invention is thus an original adaptation of the standards applicable to axial implants, to the emplacement of lateral insertion implants.

In the systems dedicated to axial implants, the function of the surgical guide 1 is to monitor and control the drilling direction and depth, that is to say to exert an axial guidance and an axial stability, but only in a single direction (depth). The surgical guide adapted to the lateral insertion implants should monitor and control the height position of the osteotomy plane with respect to the alveolar ridge, that is to say should block the milling cutter in the two axial directions.

The drilling barrels according to the invention are thus different from conventional barrels: since the milling cutter is blocked axially, it has to be inserted in a perpendicular direction, which means that the barrels are open laterally. Consequently the bores 9 and the inserts 10 are not cylindrical, but are also open laterally; the inserts 10 are in particular in the shape of a bracket. However, the external dimensions of each insert are compatible with the normal dimensions of the guide cylinders used in the templates 8 intended for the emplacement of the axial implants.

The milling cutter 4 is no longer a standard milling cutter, but is necessarily provided with axial support means. This specific milling cutter 4 is produced by forging a single piece of stainless steel of type Z33C13.

The procedure for inserting an axial implant in situ normally involves introducing the implant by means of an implant carrier into the previously made osteotomy. It is known to use the cylinder of the template in order to guide a special implant carrier.

In the case of lateral insertion implants, these are introduced by percussion into their bone sites. Thanks to its inserts 10, the surgical template 1 is advantageously used to guide their insertion in situ. These implants are those most commonly used for a lateral insertion, that is to say those comprising a disc-shaped base surmounted by a shank onto which is screwed the prosthesis.

The accuracy of the osteotomies carried out with the surgical guide according to the invention permits the emplacement of "disc implants" without play. Under these conditions it is not necessary to wait for the implant to bond firmly to the bony material, and the prostheses are immediately inserted in situ. This clearly represents a considerable advantage for the patient.

It goes without saying that the invention is not restricted just to the preferred embodiments described above, but on the contrary covers all the possible variants of implementation that do not go beyond the scope of the present invention as defined by the following claims.

The invention claimed is:

1. Custom-fit implant surgery guide (1) and associated milling cutter (4), of the type placed in the manner of a saddle on the alveolar ridge (7) of a maxillary or mandibular arch (2), and comprising at least one drilling barrel (11) capable of axially guiding said milling cutter (4), characterized in that said barrel (11) is open laterally and in that at least a part of the internal surface (17) of said barrel (11) and at least a part of the external surface of said milling cutter (4) co-operate with one another and ensure the total axial stability of said milling cutter (4) with respect to said barrel (11).

2. Custom-fit implant surgery guide (1) and associated milling cutter (4) according to claim 1, characterized in that the barrel (11) comprises a transverse slit (12) extending in a substantially medial plane perpendicular to its axis (YY') and in that a drive shaft (4) of said milling cutter (4) comprises a collar (13), said slit (12) and said collar (13) co-operating with one another.

3. Custom-fit implant surgery guide (1) and associated milling cutter (4) according to claim 1, characterized in that a drive shaft (14) of said milling cutter (4) comprises two collars (13) surrounding said barrel (11).

4. Custom-fit implant surgery guide (1) and associated milling cutter (4) according to claim 3, characterized in that the internal surface (17) of the barrel (11) comprises a radially grooved part (30) and in that said drive shaft (14) of said milling cutter (4) comprises a ringed part (29), said grooved part (30) and said ringed part (29) being complementary and co-operating with one another.

5. Custom-fit implant surgery guide (1) and associated milling cutter (4) according to claim 1, characterized in that the barrel (11) extends laterally in a direction substantially perpendicular to the longitudinal axis of said guide (1).

6. Custom-fit implant surgery guide (1) and associated milling cutter (4) according to claim 1, characterized in that at least a part of a drive shaft (14) of said milling cutter (4) itself acts as a milling cutter and has longitudinal splines (16) whose edges are cutting edges.

7. Custom-fit implant surgery guide (1) and associated milling cutter (4) according to claim 1, characterized in that said milling cutter (4) comprises at least one toothed wheel (15).

8. Custom-fit implant surgery guide (1) and associated milling cutter (4) according to claim 1, characterized in that said guide (1) has at least one laterally open bore (9) comprising an insert (10), and in that at least a part of the internal surface (23) of said insert (10) and a part of the external surface (20) of said barrel (11) co-operate with one another and ensure the axial stability of said barrel (11) with respect to said bore (9).

9. Custom-fit implant surgery guide (1) and associated milling cutter (4) according to claim 8, characterized in that the internal surface (23) of the insert (10) comprises a groove (22) extending in a substantially medial plane perpendicular to its axis and in that the external surface (20) of the barrel (11) comprises a medial spline (21) complementary to said groove (22).

10. Custom-fit implant surgery guide (1) and associated milling cutter (4) according to claim 8, characterized in that the barrel (11) and the insert (10) have the general shape of a bracket, the cross-section of which is substantially U-shaped and includes branches 18, said branches (18) of the U extending substantially laterally in a plane parallel to the ridge (7), and the axis (YY') perpendicular to said ridge (7) passing through the center of the rounded part of the U coinciding with the axis of said milling cutter (4).

11. Custom-fit implant surgery guide (1) and associated milling cutter (4) according to claim 8, characterized in that:
the insert (10) preferably has a length of 8.00 mm, a height of 5.00 mm, a first semi-cylindrical internal surface (23) with a diameter of 4.50 mm, a first semi-cylindrical external surface (24) with a diameter of 6.00 mm, first branches (25) of thickness 0.75 mm, an internal groove (22) of rectangular cross-section of depth 0.43 mm and width 1.05 mm, the barrel (11) preferably has a length of 14.25 mm, a height of 5.00 mm, a second semi-cylindrical internal surface (17) of diameter 1.54 mm, a second semi-cylindrical external surface (20) of diameter 4.50 mm, second branches (18) of thickness 1.48 mm, an external spline (21) of rectangular cross-section 0.43 mm high and 1.00 mm wide, a transverse slit (12) preferably has a width of 0.33 mm, a drive shaft (14) preferably has a diameter of 1.50 mm and a height of 13.75 mm between a collar (13) and the end (26) intended to be integral with the drive device, and a height of the order of 8.75 mm, 14.75 mm or 20.75 mm between said collar (13) and the end supporting the a toothed wheel (15), said collar or collars (13) preferably has/have a diameter of 3.50 mm and a thickness of 0.30 mm, said toothed wheel (15) preferably has a diameter of 3.05 mm, 6.05 mm, 7.05 mm, 8.05 mm, 9.05 mm, 10.05 mm, 12.05 mm, 15.05 mm or 20.05 mm, and a thickness of 0.30 mm.

12. Method for producing a custom-fit implant surgery guide (1) and associated milling cutter (4) according to claim 1, said method being of the type comprising the following stages:
a) placing a scannographic guide in the patient's mouth,
b) acquisition by computer of the scanner data of said scannographic guide and of said patient's mandible (2) or maxilla,
c) computer simulation of said mandible (2) or said maxilla using the said data,
d) computer generation, under the control of the dental surgeon, of implant plan parameters using said simulation,
e) computer control, using said plan parameters, of a device for making a template (8) intended to reproduce the shape of the alveolar ridge (7) and exhibiting bores (9) having precalculated axes (XX', YY', ZZ') and positions,
f) fixing guide inserts (10) in said bores (9),
g) inserting in said inserts (10) drilling barrels (11) arranged so as to control the direction and depth of penetration of a milling cutter (4), characterized in that said implant plan is adapted for lateral insertion implants with respect to the alveolar ridge (7),
said bores (9), said inserts (10) and said barrels (11) are provided with lateral openings with respect to said ridge (7), and
said milling cutter (4) is provided with axial support means (13, 27, 28) co-operating with said barrels (11).

13. Method for producing the custom-fit implant surgery guide (1) and associated milling cutter (4) according to claim 12, characterized in that the inserts (10) and the barrels (11) are made respectively of titanium alloy, preferably TA6V, and of steel, preferably INOX 316L.

14. Method for producing the custom-fit implant surgery guide (1) and associated milling cutter (4) according to claim 12, characterized in that the template (8) is made by stereolithography.

15. Method for producing the custom-fit implant surgery guide (1) and associated milling cutter (4) according to claim 12, characterized in that the inserts (10) are bonded to the template (8).

16. Method for producing the custom-fit implant surgery guide (1) and associated milling cutter (4) according to claim 12, characterized in that said milling cutter (4) is made by forging a single piece of metal in the course of a specific stage.

17. Use of the custom-fit implant surgery guide (1) and associated milling cutter (4) according to claim 1 in a process for the emplacement of dental implants, of the type of those comprising the following stages:
- a) placing a scannographic guide in the patient's mouth,
- b) acquisition by computer of the scanner data of said scannographic guide and of said patient's mandible (2) or maxilla,
- c) computer simulation of said mandible (2) or said maxilla using the scanner data,
- d) computer generation, under the control of the dental surgeon, of implant plan parameters using said simulation,
- e) computer control, using said plan parameters, of a device for making a template (8) intended to reproduce the shape of the alveolar ridge (7) and exhibiting bores (9) having precalculated axes (XX', YY', ZZ') and positions,
- f) fixing guide inserts (10) in said bores (9),
- g) inserting in said inserts (10) drilling barrels (11) arranged so as to control the direction and depth of penetration of a milling cutter (4),
- h) formation by means of said milling cutter (4) guided by said barrels (11) of osteotomies (3) intended to receive said implants in said mandible (2) or said maxilla,
- I) placement between said inserts (10) of said implants into said osteotomies (3), characterized in that:
  the plan is adapted to lateral insertion implants with respect to the alveolar ridge (7), and
  the milling cutter (4) is introduced laterally with respect to said ridge (7) into said barrels (11).

18. Use of the custom-fit implant surgery guide (1) and associated milling cutter (4) according to claim 17, characterized in that the implants are introduced by percussion into the osteotomies (3) while being guided laterally with respect to the ridge (7) by the inserts (10).

19. Use of the custom-fit implant surgery guide (1) and associated milling cutter (4) according to claim 17, characterized in that the implants are of the type comprising at least one disc arranged axially on a shank intended to carry a prosthesis.

20. Use of the custom-fit implant surgery guide (1) and associated milling cutter (4) according to claim 17, characterized in that the implants are loaded by the prostheses immediately after their emplacement in situ.

* * * * *